United States Patent
DeLuca et al.

(10) Patent No.: US 8,987,235 B2
(45) Date of Patent: Mar. 24, 2015

(54) N-CYCLOPROPYL-(20R)-2-METHYLENE-19, 26,27-TRINOR-25-AZA-VITAMIN D ANALOGS AND THEIR USES

(75) Inventors: Hector F. DeLuca, Deerfield, WI (US); Margaret Clagett-Dame, Deerfield, WI (US); Lori A. Plum, Arena, WI (US); Grazia Chiellini, Madison, WI (US)

(73) Assignee: Wisconsin Alumni Research Foundation, Madison, WI (US)

( * ) Notice: Subject to any disclaimer, the term of this patent is extended or adjusted under 35 U.S.C. 154(b) by 261 days.

(21) Appl. No.: 13/473,259

(22) Filed: May 16, 2012

(65) Prior Publication Data

US 2012/0309713 A1 Dec. 6, 2012

Related U.S. Application Data

(60) Provisional application No. 61/487,057, filed on May 17, 2011.

(51) Int. Cl.
| | | |
|---|---|---|
| A61K 31/59 | (2006.01) | |
| C07C 401/00 | (2006.01) | |
| C07C 211/03 | (2006.01) | |
| C07C 271/24 | (2006.01) | |
| C07C 215/42 | (2006.01) | |
| C07C 225/10 | (2006.01) | |
| C07F 7/18 | (2006.01) | |

(52) U.S. Cl.
CPC ............. C07C 401/00 (2013.01); C07C 271/24 (2013.01); C07C 215/42 (2013.01); C07C 225/10 (2013.01); C07C 2101/02 (2013.01); C07C 2101/14 (2013.01); C07C 2102/24 (2013.01); C07F 7/1856 (2013.01)
USPC ............................ 514/167; 552/653; 564/454

(58) Field of Classification Search
USPC ............................ 552/653; 514/167; 564/454
See application file for complete search history.

(56) References Cited

U.S. PATENT DOCUMENTS

| | | | |
|---|---|---|---|
| 4,217,288 | A | 8/1980 | DeLuca et al. |
| 4,481,198 | A | 11/1984 | DeLuca et al. |
| 4,666,634 | A | 5/1987 | Miyamoto et al. |
| 4,800,198 | A | 1/1989 | DeLuca et al. |
| 4,866,048 | A | 9/1989 | Calverley et al. |
| 5,086,191 | A | 2/1992 | DeLuca et al. |
| 5,089,641 | A | 2/1992 | DeLuca et al. |
| 5,366,731 | A | 11/1994 | DeLuca et al. |
| 5,494,905 | A | 2/1996 | Hesse et al. |
| 5,536,713 | A | 7/1996 | DeLuca et al. |
| 5,686,435 | A | 11/1997 | Hesse et al. |
| 5,756,733 | A | 5/1998 | Hesse et al. |
| 5,786,347 | A | 7/1998 | Hesse et al. |
| 5,843,928 | A | 12/1998 | Deluca et al. |
| 5,872,140 | A | 2/1999 | Hesse et al. |
| 5,945,410 | A | 8/1999 | DeLuca et al. |
| 6,013,814 | A | 1/2000 | Hesse et al. |
| 6,566,352 | B1 | 5/2003 | DeLuca et al. |
| 6,579,861 | B2 | 6/2003 | DeLuca et al. |
| 6,600,058 | B1 | 7/2003 | Steinmeyer et al. |
| 6,613,920 | B1 | 9/2003 | Steinmeyer et al. |
| 6,627,622 | B2 | 9/2003 | DeLuca et al. |
| 6,642,218 | B2 | 11/2003 | Steinmeyer et al. |
| 7,211,680 | B2 | 5/2007 | Steinmeyer et al. |
| 7,235,552 | B1 | 6/2007 | Hesse et al. |

FOREIGN PATENT DOCUMENTS

WO  WO 2006032299  *  3/2006

OTHER PUBLICATIONS

Jinge Zhu et al, Screening of Selective Inhibitors of 1 [alpha],25-Dihyroxyvitamin D3 24-Hydroxylase Using Recombinant Human Enzyme Expressed in *Escherichia coli*, Biochemistry, vol. 49, No. 49, pp. 10403-10411, Dec. 2010.
International Search Report and Written Opinion, PCT International Application No. PCT/US2012/038134, mailed Sep. 4, 2012.
International Preliminary Report on Patentability and Written Opinion, PCT International Application No. PCT/US2012/038134, dated Nov. 19, 2013.
Perlman et al, 1alpha,25-dihyroxyvitamin D3, A Novel Vitamin D-related Compound with Potential Therapeutic Activity, Tetrahedron Letters, vol. 31, No. 13, pp. 1823-1824, 1990.
Perlman et al, Novel Synthesis of 19-Nor-Vitamin D Compounds, Tetrahedron Letters, vol. 32, No. 52, pp. 7663-7666, 1991.
Okano et al, Regulatory Activites of 2beta-(3-Hydroxypropoxy)-1alpha,25-Dihydroxyvitamin D3, A Novel Synthetic Vitamin D3 Derivative, on Calcium Metabolism, Biochem. Biophys. Res. Commun., vol. 163, No. 3, pp. 1444-1449, Sep. 29, 1989.
Miyamoto et al, Synthetic Studies of Vitamin D Analogs. XIV. Synthesis and Calcium Regulating Activity of Vitamin D3 Analogs Bearing a Hydroxyalkoxy Group at the 2beta-Position, Chem. Pharm. Bull., vol. 41, No. 6, pp. 1111-1113, Jun. 1993.
Posner et al, Stereocontrolled Total Synthesis of Calcitrol Derivatives: 1,25-Dihyroxy-2-(4'-hydroxybutyl)vitamin D3 Analogs of an Osteoporosis Drug, J. Org. Chem., vol. 59, pp. 7855-7861, 1994.

(Continued)

*Primary Examiner* — Barbara P Badio
(74) *Attorney, Agent, or Firm* — Andrus Intellectual Property Law, LLP

(57) ABSTRACT

This invention discloses N-cyclopropyl-(20R)-2-methylene-19,26,27-trinor-25-aza-vitamin D analogs, and specifically N-cyclopropyl-(20R)-2-methylene-19,26,27-trinor-25-aza-1α-hydroxyvitamin $D_3$ and pharmaceutical uses therefor. This compound exhibits relatively high binding activity and pronounced activity in arresting the proliferation of undifferentiated cells and inducing their differentiation to the monocyte thus evidencing use as an anti-cancer agent especially for the treatment or prevention of leukemia, colon cancer, breast cancer, skin cancer or prostate cancer.

28 Claims, 5 Drawing Sheets

(56) References Cited

OTHER PUBLICATIONS

Posner et al, 2-Fluoroalkyl A-Ring Analogs of 1,25-Dihyroxyvitamin D3. Stereocontrolled Total Synthesis via Intramolecular and Intermolecular Diels-Alder Cycloadditions. Preliminary Biological Testing, J. Org. Chem., vol. 60, pp. 4617-4626, 1995.

Lythgoe et al, Calciferol and its Relatives. Part 22. A Direct Total Synthesis of Vitamin D2 and Vitamin D3. J. Chem. Soc. Perkin I., pp. 590, 1978.

Lythgoe, Synthetic Approaches to Vitamin D and its Relatives. Chem. Soc. Rev., vol. 9, pp. 449, 1983.

Toh et al, Studies on a Convergent Route to Side-Chain Analogues of Vitamin D:25-Hydroxy-23-oxavitamin D3. J. Org. Chem., vol. 48, pp. 1414-1417, 1983.

Baggiolini et al, Stereocontrolled Total Synthesis of 1 [alpha],25-Dihydroxycholecaliferol and 1 [alpha],25-Dihydroxyergocalciferol. J. Org. Chem., vol. 51, pp. 3098-3108, 1986.

Sardina et al, Studies on the Synthesis of Side-Chain Hydroxylated Metabolites of Vitamin D. 2. Stereocontrolled Synthesis of 25-Hydroxyvitamin D2. J. Org. Chem., vol. 51, pp. 1264-1269, 1986.

Collins et al, Normal Functional Characteristics of Cultured Human Promyelocytioc Leukemia Cells (HL-60) After Induction of Differentiation by Dimethylsulfoxide. The Journal of Experimental Medicine., vol. 149, pp. 969-974, 1979.

Arbour et al, A Highly Sensitive Method for Large-Scale Measurements of 1,25-Dihydroxyvitamin D. Analytical Biochem., vol. 255, pp. 148-154, 1998.

Suda et al, Biological Activity of 25-Hydroxyergocalciferal in Rats. J. Nutrition., vol. 100, pp. 1049-1052, 1970.

* cited by examiner

N-CYCLOPROPYL-(20R)-2-METHYLENE-19,26, 27-TRINOR-25-AZA-VITAMIN D ANALOGS AND THEIR USES

CROSS REFERENCE TO RELATED APPLICATIONS

This application claims the benefit of U.S. Provisional Application No. 61/487,057, filed May 17, 2011, which is incorporated by reference herein in its entirety for any purpose.

BACKGROUND OF THE INVENTION

This invention relates to vitamin D compounds, and more particularly to N-cyclopropyl-(20R)-2-methylene-19,26,27-trinor-25-aza-vitamin D analogs and their pharmaceutical uses, and especially N-cyclopropyl-(20R)-2-methylene-19,26,27-trinor-25-aza-1α-hydroxyvitamin $D_3$, its biological activities, and its pharmaceutical uses.

The most active metabolite of vitamin $D_3$, namely, 1α,25-dihydroxyvitamin $D_3$, is a potent calcium and phosphorous regulating hormone playing an important role in bone homeostasis in animals and humans. Also, in addition to this classical role, the natural hormone elicits immunomodulation as well as cell differentiation and proliferation activities in numerous malignant cells and keratinocytes [Feldman et al, Vitamin D, $2^{nd}$ ed,; Elsevier Academic Press: New York, 2005]. 1α,25-Dihydroxyvitamin $D_3$ expresses these functions by binding to the vitamin D receptor (VDR), a ligand-regulated transcription factor. Structural analogs of this metabolite have been prepared and tested such as 1α-hydroxyvitamin $D_3$, 1α-hydroxyvitamin $D_2$, and various other side-chain and A-ring modified vitamins. Some potent synthetic analogs have been used clinically to treat bone disorders such as osteoporosis and the skin disorder—psoriasis. Some of these compounds exhibit separation of activities in cell differentiation and calcium regulation. The difference in activity may be advantageous in treating a variety of diseases such as renal osteodystrophy, vitamin D-resistant rickets, osteoporosis, and malignancies.

In U.S. Pat. Nos. 4,800,198, 5,089,641 and 5,366,731, a class of secosterol compounds has also been prepared which exhibit high growth inhibitory activity towards malignant cells, such as leukemia cells, but have significantly less of the undesired side-effects (potent calcemic action) of some of the known vitamin D compounds mentioned above. This selectivity and specificity of action makes the secosterols potentially useful as agents for the treatment of malignancies such as leukemia. These secosterol compounds have also been proposed for use in dermatological compositions to treat skin disorders such as dermatitis, eczema and psoriasis, as well as in cosmetic compositions to treat less sever skin conditions such as wrinkles, lack of dermal hydration, i.e. dry skin, lack of adequate skin firmness, i.e. skin slackness, and insufficient sebum secretion.

Calcipotriene is another synthetic vitamin $D_3$ derivative that is marketed for topical dermatological use against psoriasis. Calcipotriene has a 24-cyclopropyl substituent, and is disclosed in U.S. Pat. No. 4,866,048.

Another class of vitamin D analogs, i.e. the so called 19-nor-vitamin D compounds, is characterized by the replacement of the A-ring exocyclic methylene group (carbon 19), typical of the vitamin D system, by two hydrogen atoms. Biological testing of 19-nor-analogs such as 1α,25-dihydroxy-19-nor-vitamin $D_3$ revealed a selective activity profile with high potency in inducing cellular differentiation, and reduced calcium mobilizing activity. Thus, these compounds may be potentially useful as therapeutic agents for the treatment of malignancies, or the treatment of various skin disorders. Two different methods of synthesis of such 19-nor-vitamin D analogs have been described (Perlman. et al., Tetrahedron Lett. 31, 1823 (1990); Perlman et al., Tetrahedron Lett. 32, 7663 (1991), and DeLuca et al., U.S. Pat. No. 5,086,191).

In U.S. Pat. No. 4,666,634, 2β-hydroxy and alkoxy (e.g., ED-71) analogs of 1α,25-dihydroxyvitamin $D_3$ have been described and examined by Chugai group as potential drugs for osteoporosis and as antitumor agents. See also Okano et al., Biochem. Biophys. Res. Commun. 163, 1444 (1989). Other 2-substituted (with hydroxyalkyl, ED-120, and fluoroalkyl groups) A-ring analogs of 1α,25-dihydroxyvitamin $D_3$ have also been prepared and tested (Miyamoto et al., Chem. Pharm. Bull. 41, 1111 (1993) Nishii et al., Osteoporosis Int. Suppl. 1, 190(1993); Posner et al., J. Org. Chem, 59, 7855 (1994), and J. Org. Chem, 60, 4617 (1995)).

2-substituted analogs of 1α,25-dihydroxy-19-nor-vitamin $D_3$ have also been synthesized, i.e. compounds substituted at 2-position with hydroxy or alkoxy groups (DeLuca et al., U.S. Pat. No. 5,536,713), with 2-alkyl groups (DeLuca et al U.S. Pat. No. 5,945,410), and with 2-alkylidene groups (DeLuca et al U.S. Pat. No. 5,843,928), which exhibit interesting and selective activity profiles. All these studies indicate that binding sites in vitamin D receptors can accommodate different substituents at C-2 in the synthesized vitamin D analogs.

In a continuing effort to explore the 19-nor class of pharmacologically important vitamin D compounds, analogs which are characterized by the presence of a methylene substituent at carbon 2 (C-2), a hydroxyl group at carbon 1 (C-1), and a shortened side chain attached to carbon 20 (C-20) have also been synthesized and tested. 1α-hydroxy-2-methylene-19-nor-pregnacalciferol is described in U.S. Pat. No. 6,566,352 while 1α-hydroxy-2-methylene-19-nor-homopregnacalciferol is described in U.S. Pat. No. 6,579,861 and 1α-hydroxy-2-methylene-19-nor-bishomopregnacalciferol is described in U.S. Pat. No. 6,627,622. All three of these compounds have relatively high binding activity to vitamin D receptors and relatively high cell differentiation activity, but little if any calcemic activity as compared to 1α,25-dihydroxyvitamin $D_3$. Their biological activities make these compounds excellent candidates for a variety of pharmaceutical uses, as set forth in the '352, '861 and '622 patents.

SUMMARY OF THE INVENTION

The present invention is directed toward N-cyclopropyl-(20R)-2-methylene-19,26,27-trinor-25-aza-vitamin D analogs, and their pharmaceutical uses, and more specifically toward N-cyclopropyl-(20R)-2-methylene-19,26,27-trinor-25-aza-1α-hydroxyvitamin $D_3$, its biological activity, and various pharmaceutical uses for this compound.

Structurally these N-cyclopropyl-(20R)-2-methylene-19,26,27-trinor-25-aza-vitamin D analogs are characterized by the general formula I shown below:

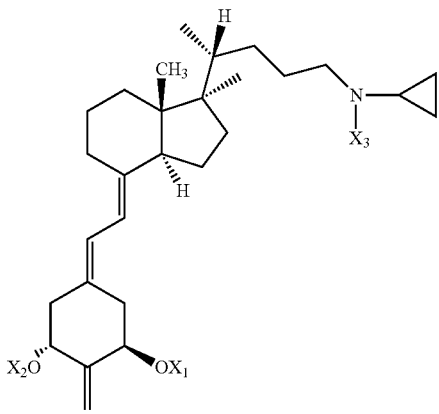

where $X_1$, $X_2$ and $X_3$, which may be the same or different, are each selected from the group consisting of hydrogen and a hydroxy-protecting group.

The preferred analog is N-cyclopropyl-(20R)-2-methylene-19,26,27-trinor-25-aza-1α-hydroxyvitamin $D_3$ (referred to herein as "CPA- 1") which has the following formula Ia:

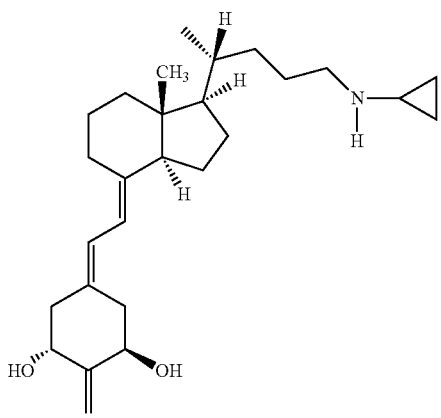

The above compounds of formula I, especially formula Ia, exhibit a desired, and highly advantageous, pattern of biological activity. These compounds are characterized by relatively high binding to vitamin D receptors, i.e. they bind with only slightly lower affinity than the natural hormone 1α,25-dihydroxyvitamin $D_3$ They are equally as potent in causing differentiation of HL-60 cells as 1,25(OH)$_2$D$_3$. They also exhibit relatively low transcriptional activity as well as relatively low activity in their ability to mobilize calcium from bone, but are quite potent in their ability to promote intestinal calcium transport, as compared to 1α,25-dihydroxyvitamin $D_3$.

The above compounds I, and particularly Ia, have relatively high binding affinity, are characterized by some cell-type selectivity and cause differentiation of cancer cells nearly as well as the native hormone but have notably lower potency in raising tissue calcium levels. Thus, these compounds, especially CPA-1, have potential as anti-cancer agents and provide therapeutic agents for the prevention or treatment of leukemia, colon cancer, breast cancer, skin cancer and prostate cancer.

One or more of the compounds may be present in a composition to treat or prevent the above-noted diseases in an amount from about 0.01 μg/gm to about 1000 μg/gm of the composition, preferably from about 0.1 μg/gm to about 500 μg/gm of the composition, and may he administered topically, transdermally, orally, rectally, nasally, sublingually, or parenterally in dosages of from about 0.01 μg/day to about 1000 μg/day, preferably from about 0.1 μg/day to about 500 μg/day.

BRIEF DESCRIPTION OF THE DRAWINGS

FIG. 1 is a graph illustrating the relative activity of CPA-1 and 1,25(OH)-$_2$D$_3$ to compete for binding with [$^3$H]-1,25-(OH)$_2$-D$_3$ to the full-length recombinant rat vitamin D receptor;

FIG. 2 is a graph illustrating the percent HL-60 cell differentiation as a function of the concentration of CPA-1 and 1,25(OH)$_2$D$_3$;

FIG. 3 is a graph illustrating the in vitro transcription activity of 1,25(OH)$_2$D$_3$ as compared to CPA-1;

FIG. 4 is a bar graph illustrating the bone calcium mobilization activity of 1,25(OH)$_2$D$_3$ as compared to CPA-1; and FIG. 5 is a bar graph illustrating the intestinal calcium transport activity of 1,25(OH)$_2$D$_3$ as compared to CPA-1.

DETAILED DESCRIPTION OF THE INVENTION

Figure 1:
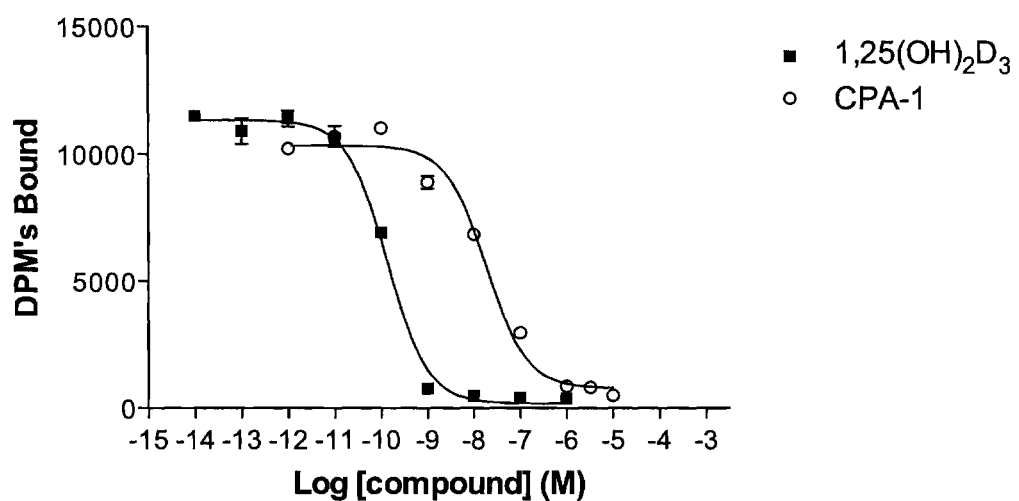
FIGS. 1-5 illustrate various biological activities of N-cyclopropyl-(20R)-2-methylene-19,26,27-trinor-25-aza-1α-hydroxyvitamin $D_3$, hereinafter referred to as "CPA-1," as compared to the native hormone 1α,25-dihydroxyvitamin $D_3$, hereinafter "1,25(OH)$_2$D$_3$."

As used in the description and in the claims, the term "hydroxy-protecting group" signifies any group commonly used for the temporary protection of hydroxy functions, such as for example, alkoxycarbonyl, acyl, alkylsilyl or alkylarylsilyl groups (hereinafter referred to simply as "silyl" groups), and alkoxyalkyl groups. Alkoxycarbonyl protecting groups are alkl-O—CO— groupings such as methoxycarhonyl, ethoxycarbonyl, propoxycarbonyl, isopropxycarbonyl, butoxycarbonyl, isobutoxycarbonyl, tert-butoxycarbonyl, benzyloxycarbonyl or allyloxycarbonyl. The term "acyl" signifies an alkanoyl group of 1 to 6 carbons, in all of its isomeric forms, or a carboxyalkanoyl group of 1 to 6 carbons, in all of its isomeric forms, or a carboxyalkanoyl group of 1 to 6 carbons, such as an oxalyl, malonyl, succinyl, glutaryl group, or an aromatic acyl group such as benzoyl, or a halo, nitro, or alkyl substituted benzoyl group. The word "alkyl" as used in the description or the claims, denotes a straight-chain or branched alkyl radical of 1 to 10 carbons, in all its isomeric forms. "Alkoxy" refers to any alkyl radical which is attached by oxygen, i.e. a group represented by "alkyl-O—." Alkoxyalkyl protecting groups are groupings such as methoxymethyl, ethoxymethyl, methoxyethoxymethyl, or tetrahydrafuranyl and tetrahydropyranyl. Preferred silyl-protecting groups are trimethylsilyl, triethylsilyl, t-butyldimethylsilyl, dibutylmethylsilyl, diphenylmethylsilyl, phenyldimethylsilyl, diphenyl-t-butylsilyl and analogous alkylated silyl radicals. The term "aryl" specifies a phenyl-, or an alkyl-, nitro- or halo-substituted phenyl group.

A "protected hydroxy" group is a hydroxy group derivatised or protected by any of the above groups commonly used for the temporary or permanent protection of hydroxy functions, e.g. the silyl, alkoxyalkyl, acyl or alkoxycarbonyl groups, as previously defined. The terms "hydroxyalkyl", deuteroalkyl" and "fluoroalkyl" refers to an alkyl radical substituted by one or more hydroxy, deuterium or fluoro groups respectively. An "alkylidene" refers to a radical having the general formula $C_kH_{2k}$— where k is an integer.

N-cyclopropyl-(20R)-2-methylene-19,26,27-trinor-25-aza-1α-hydroxyvitamin $D_3$ (referred to herein as "CPA-1"), a 19-nor vitamin D analog which is characterized by the presence of a methylene substituent at the carbon 2 (C-2), and the methyl groups normally located at the 26 and 27 positions (C-26 and C-27) as well as the hydroxyl substituent normally attached to the 25-position (C-25) in the side chain, replaced with an aza group located at carbon atom 25 (C-25) in the side chain, was synthesized and tested. Such vitamin D analog seemed an interesting target because the relatively small methylene group at the C-2 position should not interfere with binding to the vitamin D receptor. Structurally, this 19-nor analog is characterized by the general formula Ia previously illustrated herein, and its pro-drug (in protected hydroxy form) is characterized by general formula I previously illustrated herein.

The preparation of N-cyclopropyl-(20R)-2-methylene-19, 26,27-trinor-25-aza-vitamin D analogs having the structure I can be accomplished by a common general method, i.e. the condensation of a bicyclic Windaus-Gundmann type ketone II with the allylic phosphine oxide III to the corresponding 2-methylene-19-nor-vitamin D analog I followed by deprotection at positions C-1, C-3 and C-25 in the latter compound (see Schemes I and II herein):

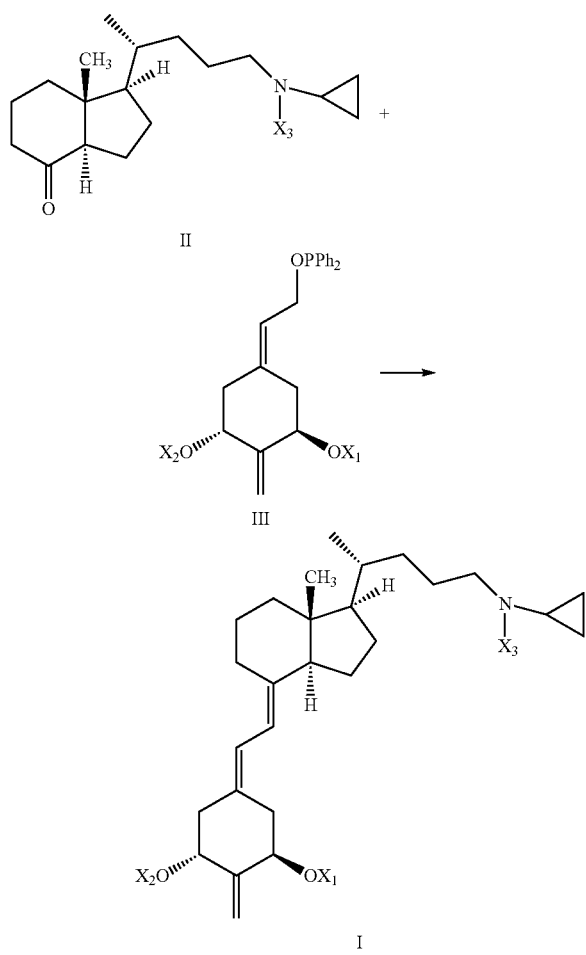

In the structures I, II and III, groups $X_1$, $X_2$ and $X_3$ are hydroxy-protecting groups, preferably $X_1$ and $X_2$ are t-butyldimethylsilyl (TBS), and $X_3$ is tert-butyloxycarbonyl (BOC), it being also understood that any functionalities that might be sensitive, or that interfere with the condensation reaction, be suitably protected as is well-known in the art. The process shown above represents an application of the convergent synthesis concept, which has been applied effectively for the preparation of vitamin D compounds [e.g. Lythgoe et al., J. Chem. Soc. Perkin Trans. I, 590 (1978); Lythgoe, Chem. Soc. Rev. 9, 449 (1983); Toh et al., J. Org. Chem. 48 1414 (1983); Baggiolini et al., J. Org. Chem, 51, 3098 (1986); Sardina et al., J. Org. Chem. 51, 1264 (1986); J. Org. Chem. 51, 1269 (1986); DeLuca et al., U.S. Pat. No. 5,086,191; DeLuca et al., U.S. Pat. No. 5,536,713.

The hydrindanone of the general structure II is not known. It can be prepared by the method shown in Schemes I and II herein (see the preparation of compound CPA-1).

For the preparation of the required phosphine oxides of general structure III, a synthetic route has been developed starting from a methyl quinicate derivative which is easily obtained from commercial (1R,3R,4S,5R)-(−)-quinic acid as described by Perlman et al., Tetrahedron Lett. 32, 7663 (1991) and DeLuca et al., U.S. Pat. No. 5,086,191.

The overall process of the synthesis of compounds I and Ia is illustrated and described more completely in U.S. Pat. No. 5,843,928 entitled "2-Alkylidene-19-Nor-Vitamin D Compounds" the specification of which is specifically incorporated herein by reference.

More specifically, reference should be made to the following illustrative example and description as well as to Schemes I and II herein for a detailed illustration of the preparation of compound CPA-1.

This invention is described by the following illustrative examples. In these examples specific products identified by Arabic numerals (e.g., 1, 2, 3, etc.) refer to the specific structures so identified in the preceding description and in the Scheme I and Scheme II.

EXAMPLES

Chemistry. Melting points (uncorrected) were determined on a Thomas-Hoover capillary melting-point apparatus. Optical rotations were measured in chloroform using a Perkin-Elmer 241 automatic polarimeter at 22° C. Ultraviolet (UV) absorption spectra were recorded with a Perkin-Elmer Lambda 3B UV-VIS spectrophotometer in ethanol. $^1$H nuclear magnetic resonance (NMR) spectra were recorded in deuteriochloroform at 200, 400 and 500 MHz with a Varian Unity, Bruker DMX-400 and Bruker DMX-500 spectrometers, respectively. $^{13}$C nuclear magnetic resonance (NMR) spectra were recorded at 50, 100 and 125 MHz with the same spectrometers in deuteriochloroform. Chemical shifts (δ) were reported downfield from internal $Me_4Si$ (δ 0.00). Electron impact (EI) mass spectra were obtained with a Micromass AutoSpec (Beverly, Mass.) instrument. High-performance liquid chromatography (HPLC) was performed on a Waters Associates liquid chromatograph equipped with a Model 6000A solvent delivery system, a Model U6K Universal injector, and a Model 486 tunable absorbance detector. THF was freshly distilled before use from sodium benzophenone ketyl under argon.

Example I

Preparation of (8S,20S)-de-A,B-20-(hydroxymethyl) pregnan-8-ol (1)

Ozone was passed through a solution of vitamin $D_2$ (3 g, 7.6 mmol) in methanol (250 mL) and pyridine (2.44 g, 2.5 mL, 31 mmol) for 50 min at −78° C. The reaction mixture was then flushed with an oxygen for 15 min to remove the residual ozone and the solution was treated with $NaBH_4$ (0.75 g, 20 mmol). After 20 min the second portion of $NaBH_4$ (0.75 g, 20 mmol) was added and the mixture was allowed to warm to room temperature. The third portion of $NaBH_4$ (0.75 g, 20 mmol) was then added and the reaction mixture was stirred for 18 h. The reaction was quenched with water (40 mL) and the solution was concentrated under reduced pressure. The residue was extracted with ethyl acetate and the combined organic phases were washed with 1M aq. HCl, saturated aq. $NaHCO_3$, dried ($Na_2SO_4$) and concentrated under reduced pressure. The residue was chromatographed on silica gel with hexane/ethyl acetate (75:25) to give the diol 1 (1.21 g, 75% yield) as white crystals:

m.p. 106-108° C.; $[\alpha]_D$+30.2° (c 1.46, $CHCl_3$); $^1H$ NMR (400 MHz, $CDCl_3$) δ 4.08 (1H, d, J=2.0 Hz, 8α-H), 3.63 (1H, dd, J=10.5, 3.1 Hz, 22-H), 3.38 (1H, dd, J=10.5, 6.8 Hz, 22-H), 1.99 (1H, br.d, J=13.2 Hz), 1.03 (3H, d, J=6.6 Hz, 21-$H_3$), 0.956 (3H, s, 18-$H_3$); $^{13}C$ NMR (100 MHz) δ 69.16 (d, C-8), 67.74 (t, C-22), 52.90 (d), 52.33 (d), 41.83 (s, C-13), 40.19 (t), 38.20 (d), 33.53 (t), 26.62 (t), 22.54 (t), 17.36 (t), 16.59 (q, C-21), 13.54 (q, C-18); MS (EI) m/z 212 (2, $M^+$), 194 (34, $M^+$—$H_2O$), 179 (33, $M^+$—$H_2O$—$CH_3$), 163 (18, $M^+$—$CH_2OH$—$H_2O$), 135 (36), 125 (54), 111 (100), 95 (63), 81 (67); exact mass calculated for $C_{13}H_{22}O$ ($M^+$—$H_2O$) 194.1671, found 194.1665.

Preparation of (8S,20S)-de-A,B-8-triethylsilyloxy-20-(acetyloxymethyl)pregnane (2)

Acetic anidryde (0.41 g, 0.40 mL, 4.0 mmol) was added to a solution of the diol 1 (0.5 g, 2.3 mmol) and $Et_3N$ (1.64 mL, 11.7 mmol) in anhydrous $CH_2Cl_2$ (20 mL) at room temperature (rt). The reaction mixture was stirred at rt for 24 h, diluted with methylene chloride (100 mL), washed with 5% aq. HCl, water, saturated aq. $NaHCO_3$, dried ($Na_2SO_4$) and concentrated under reduced pressure. The residue (0.68 g) was chromatographed on silica gel with hexane/ethyl acetate (75:25) to give the desired alcohol (0.53 g, 88% yield) as a colorless oil.

To a stirred solution of the alcohol (0.53 g, 2.1 mmol) and 2,6-lutidine (0.29 mL, 0.26 g, 2.5 mmol) in anhydrous methylene chloride (5 mL) triethylsilyl trifluoromethane-sulfonate (0.54 mL, 2.5 mmol) was added at 0° C. The reaction mixture was allowed to warm to room temperature (1 h), and stirring was continued for additional 30 min. Methylene chloride was added and the mixture was washed with water, dried ($Na_2SO_4$) and concentrated under reduced pressure. The residue was chromatographed on silica gel with hexane/ethyl acetate (97:3) to afford the product 2 (0.74 g, 95% yield) as a color less oil:

$[\alpha]_D$+40.77 (c 4.9, $CHCl_3$); $^1H$ NMR (400 MHz, $CDCl_3$) δ 4.06 (2H, m), 3.77 (1H, dd, J=10.64, 3.08 Hz, 22-H), 2.05 (3H, s), 1.93 (1H, br. d, J=12.4 Hz), 0.98 (3H, d, J=6.6 Hz, 21-$H_3$), 0.96 (9H, t, J=7.9 Hz), 0.92 (3H, s), 0.56 (6H, q, J=7.9 Hz); $^{13}C$ NMR (100 MHz) δ 171.4, 69.61, 69.25, 53.44, 52.85, 42.26, 40.64, 35.39, 34.62, 26.80, 23.07, 21.03, 17.67, 17.09, 13.57, 6.95, 4.96; exact mass calculated for $C_{19}H_{35}O_3Si$ (M —C2H5) 339.2355, found 339.2347.

Preparation of (8S,20S)-de-A,B-8-triethylsityloxy-20-(hydroxymethyl)pregnane (3).

The acetate 2 (0.58 g, 1.6 mmol) was treated with a solution of NaOH (1 g, 25 mmol) in anhydrous ethanol (20 mL) at room temperature. After stirring of the reaction mixture for 3 h, ice and 5% aq. HCl were added until pH=6. The solution was extracted with ethyl acetate (3×50 mL) and the combined organic phases were washed with saturated aq. $NaHCO_3$, dried ($Na_2SO_4$) and concentrated under reduced pressure. The residue was chromatographed on silica gel with hexane/ethyl acetate (75:25) to give the alcohol 3 (0.44 g, 84% yield) as a colorless oil.

$[\alpha]_D$+41.1 (c 2.85, $CHCl_3$); $^1H$ NMR (400 MHz, $CDCl_3$+TMS) δ 4.04 (1H, d, J=2.4 Hz, 8α-H), 3.63 (1H, dd, J=10.5, 3.2 Hz, 22-H), 3.38 (1H, dd, J=10.5, 6.8 Hz, 22-H), 1.94 (1H, br.d, J=12.4 Hz), 1.02 (3H, d, J=6.6 Hz, 21-$H_3$), 0.95 (9H, t, J=7.9 Hz), 0.92 (3H, s, 18-$H_3$), 0.55 (6H, q, J=7.9 Hz); $^{13}C$ NMR (100 MHz) δ 69.24, 67.93, 53.07, 52.84, 42.11, 40.61, 38.27, 34.58, 26.79, 23,03, 17.63, 16.64, 13.55, 6.91, 4.90; exact mass calculated for $C_{19}H_{38}O_2Si$ ($M^+$) 326.2641, found 326.2626.

Preparation of (8S,20S)-de-A,B-8-triethylsiloxy-20-formylpregnane (4)

To a solution of DMSO (1.2 mL) in $CH_2Cl_2$ (2 mL) at −60° C. oxalyl chloride (1.11 g, 8.74 mmol) was added. After 2 min, a solution of the primary alcohol 3 (0.22 g, 0.67 mmol) in anhydrous $CH_2Cl_2$ (2 mL) at −60° C. was added via cannula. The resulting mixture was stirred at −60° C. for 2 h, quenched with $Et_3N$ (4.9 mL), and warmed up to room temperature. Upon dilution with $H_2O$, the mixture was extracted with $CH_2Cl_2$, dried ($MgSO_4$), filtered, concentrated, and purified by flash column chromatography (9.5:0.5 Hexane/EtoAc; Rf=0.12) to give the desired aldehyde 4 (0.120 mg, 0.37 mmol, 54% yield) as an oil.

$^1H$ NMR (200 MHz, $CDCl_3$) δ 9.57 (1H, d, J=3.0 Hz, CHO), 4.06 (1H, d, J=2.4 Hz, 8α-H), 2.38 (1H, m, 20-H), 1.09 (3H, d, J=6.8 Hz, 21-$H_3$), 0.95 (12H, m, $Si(CH_2CH_3)_3$+18-$H_3$), 0.55 (6H, q, J=7.8 Hz, $Si(CH_2CH_3)_3$).

Preparation of (8S,20S)-de-A,B-8-triethyisilyloxy-20-[2-(methoxycarbonyl)-et-(1E)-en-yl]pregnane (5)

To a solution of the aldehyde 4 (0.120 g, 0.37 mmol) in absolute EtOH (3 mL) at 0° C. was added methyl(triphenylphosphoranylidene)-acetate (0.307 g, 0.92 mmol) and $Et_3N$ (0.037 g, 0.37 mmol). The mixture was stirred at r.t. for 24 h and then the solvent was evaporated. The residue was purified by flash column chromatography (9.5:0.5 Hexane/EtOAc, Rf=0.45) to obtain 5 (0.105 g, 0.27 mmol, 75% yield) as an oil.

$[\alpha]_D$+58.5 (c 2.37, $CH_2Cl_2$) $^1H$ NMR (400 MHz, $CDCl_3$±TMS) δ 6.83 (1H, dd, J=15.06, 8.96, Hz), 5.73 (1H, d, J=15.6 Hz), 4.03 (1H, d, J=2.4 Hz, 8α-H), 3.76 (3H, s) 1.94 (1H, br.d, J=12.4 Hz), 1.05 (3H, d, J=6.6 Hz, 21-$H_3$), 0.95 (12H, m), 0.55 (6H, q, J=7.9 Hz); $^{13}C$ NMR (100 MHz) δ 167.56, 155.28, 118.41, 69.22, 55.54, 52.89, 51.35, 42.44, 40.63, 39.41, 34.56, 27.32, 22.96, 19.08, 17.64, 13.76, 6.94, 4.91; exact mass calculated for $C_{20}H_{36}O_3Si$ ($M^+$-Et) 351.2350, found 351.2366.

Preparation of (8S,20R)-de-A,B-8-triethylsilyloxy-20-[2-(methoxycarbonyl)ethyl]pregnane (6)

A solution of the compound 5 (0.105 g, 0.27 mmol) in absolute EtOH (5 mL) was hydrogenated for 9 h in the presence of 10% palladium on powdered charcoal (15 mg). The reaction mixture was filtered through a bed of Celite with several ethanol washes, the filtrate was concentrated and the residue was chromatographed on silica gel with Hexane/EtOAc (97:3, Rf=0.47) to give the product 6 (0.092 g, 0.24 mmol, 87% yield).

$^1$H NMR (200 MHz, CDCl$_3$) δ 4.02 (1H, broad signal, 8α-H), 3.60 (2H, t, J=6.2 Hz, 24-H$_2$), 0.94 (15H, m, Si(CH$_2$CH$_3$)$_3$+18-H$_3$+21-H$_3$), 0.54 (6H, q, J=7.14 Hz, Si(CH$_2$CH$_3$)$_3$).

Preparation of (8S,2R)-de-A,B-8-triethylsilyloxy-20-(hydroxypropyl)pregnane (7)

A solution of the compound 6 (0.092 g, 0.24 mmol) in THF (1 mL), was added to a solution of LiAlH$_4$ 1M in THF (0.48 mL, 0.48 mmol) cooled at −10° C. The reaction mixture was stirred at r.t. for 3 h, then water (0.2 mL) and NaOH 1M (0.05 mL) were added, and the resulting suspension was filtered off. The evaporation of the solvent afforded the alcohol 7 (0.070 g, 0.24 mmol, 99% yield) as a clear oil.

$^1$H NMR (400 MHz, CDCl$_3$+TMS) δ 4.03 (1H, d, J=2.4 Hz, 8α-H), 3.62 (2H, m) 1.96 (1H, br.d, J=12.4 Hz), 0.95 (15H, m), 0.55 (6H, q, J=7.9 Hz); $^{13}$C NMR (100 MHz) δ, 69.40, 63.66, 56.69 53.10, 42.13, 40.79, 35.08, 34.65, 31.68, 29.69, 29,41, 27.31, 23.00, 18.60, 17.69, 13.52, 6.95, 4.95; exact mass calculated for C$_{21}$H$_{42}$O$_2$Si (M$^+$) 354.2949, found 354.2943

Preparation of (8S,20R)-de-A,B-8-triethylsityloxy-20-[3-(cyclopropylamine)propyl]pregnane (9)

To a solution of DMSO (1.2 mL) in CH$_2$Cl$_2$ (2 mL) at −60° C. oxalyl chloride (0.34 g, 2.91 mmol) was added. After 2 min, a solution of the primary alcohol 7 (0.081 g, 0.28 mmol) in anhydrous CH$_2$Cl$_2$ (2 mL) at −60° C. was added via cannula. The resulting mixture was stirred at −60° C. for 2 h, quenched with Et$_3$N (4.9 mL), and warmed up to room temperature. Upon dilution with H$_2$O, the mixture was extracted with CH$_2$Cl$_2$, dried (MgSO$_4$), filtered, concentrated, and purified by flash column chromatography (9.5:0.5 Hexane/EtOAc; Rf=0.55) to give the desired aldehyde 8 (0.046 mg, 0.16 mmol, 57% yield) which was immediately used for the next step.

$^1$H NMR (200 MHz, CDCl$_3$) δ 9.76 (1H, s, CHO), 4.02 (1H, br signal, 8α-H), 2.40 (2H, m, 23-H$_2$), 0.94 (15H, m, Si(CH$_2$CH$_3$)$_3$+18-H$_3$+21-H$_3$), 0.54 (6H, q, J=8.05 Hz, Si(CH$_2$CH$_3$)$_3$).

To a solution of the aldehyde 8 (0.046 g, 0.16 mmol) in anhydrous CH$_2$Cl$_2$ (1 mL) was added cyclopropylamine (0.0092 g, 0.16 mmol) and the mixture was cooled at 0° C. before adding sodium triacethoxyborohydride (0.047 g, 0.22 mmol). The reaction mixture was stirred at r.t. for 2 h. Then sat. aq. NaHCO$_3$ solution (1 mL) was added and the mixture was extracted with EtOAc. The organic phase was dried (MgSO$_4$), filtered, and the solvent was evaporated to give 9 (0.049 g, 0.15 mmol, 93% yield).

[α]$_D$+44.5 (c 1.12, CH$_2$Cl$_2$); $^1$H NMR (400 MHz, CDCl$_3$+TMS) δ 4.02 (1H, d, J=2.4 Hz, 8α-H), 2.65 (2H, m), 2.13 (1H, m), 0.95 (9H, t, J=7.9 Hz), 0.89 (6H, m), 0.55 (6H, q, J=7.9 Hz), 0.43 (2H, m), 0.36 (2H, m); $^{13}$C NMR (100 MHz) δ, 69.40, 56.70, 53.09, 50.21, 42.11, 40.78, 35.20, 34.65, 33.40, 30.35, 27.33, 26.45, 23.01 18.61, 17.69, 13.51, 6.95, 6.16, 6.13, 4.94; exact mass calculated for C$_{24}$H$_{48}$NOSi (MH)$^+$ 394.3505, found 394.3506.

Preparation of (8S,20R)-de-A,B-8-triethylsilyloxy-20-[3-(cyclopropyl-N-t-Boc-amine)propyl]pregnane (10)

To a solution of compound 9 (0.033 g, 0.084 mmol) in CH$_3$CN (3 mL) Boc$_2$O (0.022 g, 0.10 mmol) and DMAP (0.001 g, 0.0084 mmol) were added under vigorous stirring. After stirring at r.t. for 1 h, the mixture was diluted with EtOAc, washed with water and brine then dried over MgSO$_4$. Concentration gave the desired compound 10 (0.040 g, 0.081 mmol, 96% yield). $^1$H NMR (400 MHz, CDCl$_3$+TMS) δ 4.02 (1H, d, J=2.4 Hz, 8α-H), 3.14 (2H, m), 2.49 (1H, m), 1.95 (1H, br.d, J=124 Hz), 1.46 (9H, s), 0.94 (9H, t, J=7.9 Hz), 0.89 (6H, m), 0.73 (2H, m), 0.56 (8H, m).

Preparation of (8S,20R)-de-A,B-20-[3-(cyclopropyl-N-t-Boc-amine)propyl]pregnan-8-one (12)

The protected alcohol 10 (0.032 g, 0.065 mmol) was dissolved in anhydrous THF (5 mL) and TBAF 1M in THF (130 ρL, 0.13 mmol) was added. After 5 h of stirring at r.t. the reaction mixture was diluted with EtOAc, washed with brine, dried (MgSO$_4$) and concentrated under reduced pressure. The residue was purified by flash column chromatography on silica gel with Hexane/EtOAc (9.5:0.5) to give the alcohol 11 (0.016 g, 0.042 mmol, 65% yield). $^1$H NMR (400 MHz, CDCl$_3$+TMS) δ 4.07 (1H, s, 8α-H), 3.14 (2H, m), 2.48 (1H, m), 1.98 (1H, br.d, J=12.4 Hz), 1.46 (9H, s), 0.93 (3H, s), 0.91 (6H, m), 0.73 (2H, m), 0.57 (2H, m).

Pyridinium dichromate (0.079 g, 0.211 mmol) was added to a solution of the alcohol 11 (0.016 g, 0.042 mmol) and pyridinium p-toluenesulfonate (0.007 g, 0.030 mmol) in anhydrous CH$_2$Cl$_2$(5 ml). The resulting suspension was stirred at r.t. for 3 h. The reaction mixture was filtered through a Waters silica Sep-pack cartridge (5 g) that was further washed with Hexane/EtOAc (9.5:0.5). After removal of the solvent the ketone 12 (0.014 g, 0.037 mmol, 88% yield) was recovered as a colorless oil.

$^1$H NMR (400 MHz, CDCl$_3$+TMS) δ 3.15 (2H, m), 2.45 (2H, m), 1.46 (3H, s), 0.96 (3H, d, J=5.7 Hz), 0.73 (2H, m), 0.64 (3H, s), 0.58 (2H, m); $^{13}$C NMR (100 MHz) δ, 212.08, 156.76, 79.18, 61.94, 56.59, 49.89, 40.95, 38.95, 35.26, 32.79, 28.47, 27.47, 24.85, 24.04, 19.04 18.69, 12.48, 7.99, exact mass calculated for C$_{23}$H$_{39}$NO$_3$Na (MNa)$^+$400.2823, found 400.2821.

Preparation of N-cyclopropyl-(20R)-2-methylene-19, 26,27-trinor-25-aza-1α-hydroxyvitamin D$_3$ (15)

To a solution of phosphine oxide 13 (0.086 g, 0.148 mmol) in anhydrous THF (0.5 mL) at −20° C. was slowly added PhLi (1.7 M in di-n-butylether, 0.087 mL, 0.148 mmol) under argon with stirring. The solution turned deep orange. After 30 min the mixture was cooled at −78° C. and a precooled (−78° C.) solution of ketone 12 (0.014 g, 0.037 mmol) in at least 200 μL of anhydrous THF was slowly added. The mixture was stirred under argon at −78° C. for 3 h and at 0° C. for 18 h. Ethyl acetate was added, and the organic phase was washed with brine, dried (MgSO$_4$) and evaporated. The residue was dissolved in hexane and applied on a Waters silica Sep-Pack cartridge (2 g). The cartridge was washed with hexane and hexane/ethyl acetate (99.5:0.5) to give the 19-norvitamin 14 (0.021 g, 0.028 mmol, 76% yield).

$^1$H NMR (CDCl$_3$, 900 MHz) δ 6.20 (1H, d, J=10.8 Hz), 5.82 (1H, d, J=10.8 Hz,), 4.96 (1H, s,), 4.91 (1H, s,), 4.41 (2H, m). 3.15 (2H, m), 2.81 (1H, dm, J=12.6 Hz), 2.52 (1H dd, J=13.5, 6.3 Hz). 2.45 (1H, dd, J=12.6, 4.5 Hz), 2.32 (1H, dd, J=13.5, 2.7 Hz), 2.17 (1H, dd, J=12.6, 8.1. Hz), 1.46 (9H, s), 0.94 (3H, d, J=7.2 Hz), 0.89 (9H, s), 0.86 (9H, s,), 0.73 (2H, m), 0.58 (2H, m), 0.54 (3H, s) 0.098 (3H, s) 0.096 (3H, s), 0.073 (3H, s), 0.055 (3H, s); $^{13}$C NMR (CDCl$_3$, 200.9 MHz) δ 157.03, 153.20, 141.39, 132.99, 122.63, 116.36, 106.48, 72.75, 71.79, 56.72, 56.48, 47.84, 45.89, 40.81, 38.78, 36.14, 33.20, 28.96, 28.73, 27.92, 26.06, 23.65, 22.43, 19.04, 18.48, 18.39, 12.32, 8.49- 4.63, −4.88; exact mass calculated for $C_{44}H_{79}NO_4Si_2Na$ (MNa)$^+$764.5440, found 764.5469.

The protected vitamin 14 (0.021 g, 0.028 mmol) was dissolved in THF (2 mL) and $CH_3CN$ (2 mL). A solution of aq. 48% HF in $CH_3CN$ (1:9 ratio, 2 mL) was added at 0° C. and the resulting mixture was stirred at r.t. for 8 h. Saturated aq. $NaHCO_3$ solution was added and the reaction mixture was extracted with ethyl acetate. The combined organic phases were washed with brine, dried ($MgSO_4$) and concentrated under reduced pressure. The residue was chromatographed on silica gel EtOAc/Hexane (80:20) to give the desired final product 15 (0.008 g, 0.019 mmol, 69% yield). The vitamin 15 was further purified by HPLC [9.4×250 mm Zorbax Sil column, 4 mL/min, Hexane/2-propanol (80:20) solvent system, Rt=8.50 min).

$^1$H NMR (CDCl$_3$, 400 MHz) 6.35 (1H, d, J=11.2 Hz), 5.88 (1H, d, J=11.2 Hz,), 5.11 (1H, s,), 5.09 (1H, s,), 4.62 (2H, m), 2.87-2.80 (2H, m), 2.70-2.55 (3H, m), 2.35-2.26 (2H, m), 2.12 (1H, m), 0.93 (3H, d, J=6.3 Hz), 0.55 (3H, s), 0.42 (2H, m), 0.34 (2H, m); $^{13}$C NMR (CDCl$_3$, 100 MHz) δ 152.00, 143.39, 130.43, 124.22, 115.28, 107.69, 71.79, 70.62, 56.43, 56.30, 50.19, 45.77, 40.42, 38.17, 36.03, 33.51, 30.36, 28.94, 27.66, 26,59, 24.66, 23.48, 22.27, 18.81, 12.07, 6.22; exact mass calculated for $C_{27}H_{44}NO_2$(MH)$^+$413,3289, found 413.3297.

Scheme 1

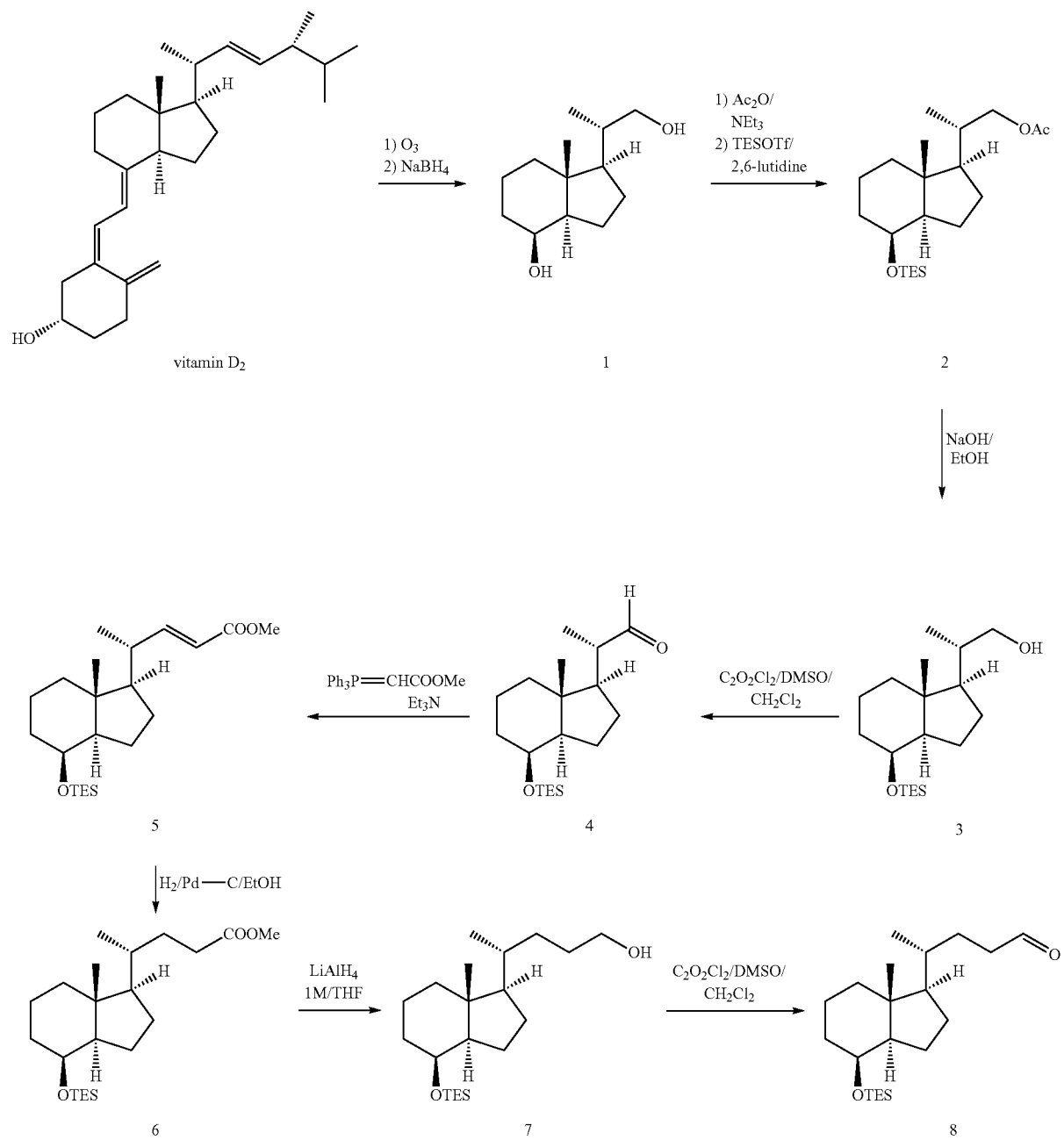

Scheme 2

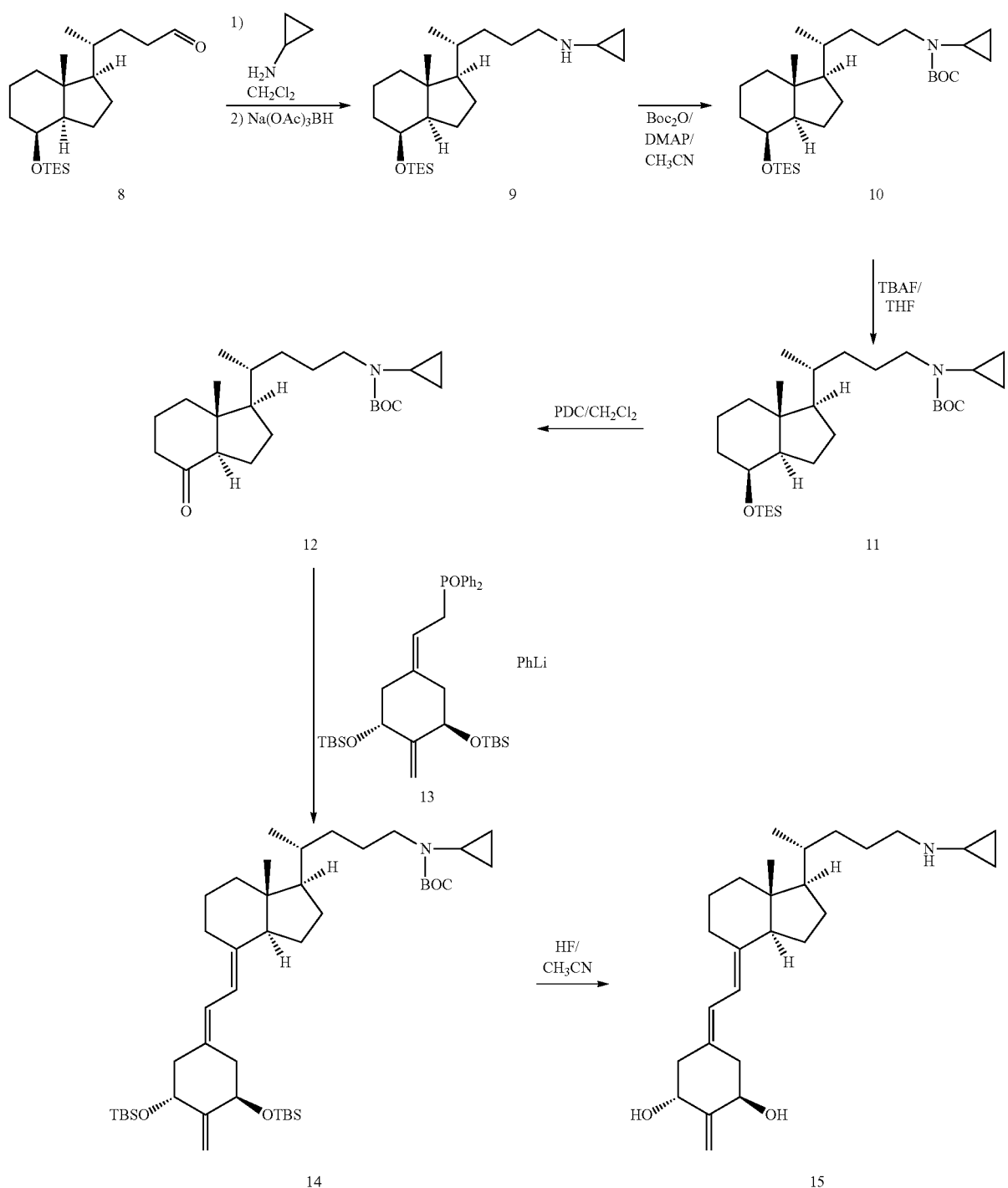

Biological Activity of CPA-1

The introduction of a methylene group to the 2-position, the removal of the methylene substituent at carbon 10, and the replacement of the methyl groups normally located at C-26 and C-27 as well as the hydroxyl group normally located at C-25 with an aza group had little effect on binding to the full length recombinant rat vitamin D receptor, as compared to 1α,25-dihydroxyvitamin $D_3$. The compound CPA-1 bound with only slightly less affinity to the receptor as compared to the standard 1,25-$(OH)_2D_3$ (FIG. 1), i.e. merely two logs (20 times) lower affinity compared to 1,25$(OH)_2D_3$. It might be expected from these results that compound CPA-1 would have equivalent biological activity. Surprisingly, however, compound CPA-1 is a highly selective analog with unique biological activity.

Figure 5:
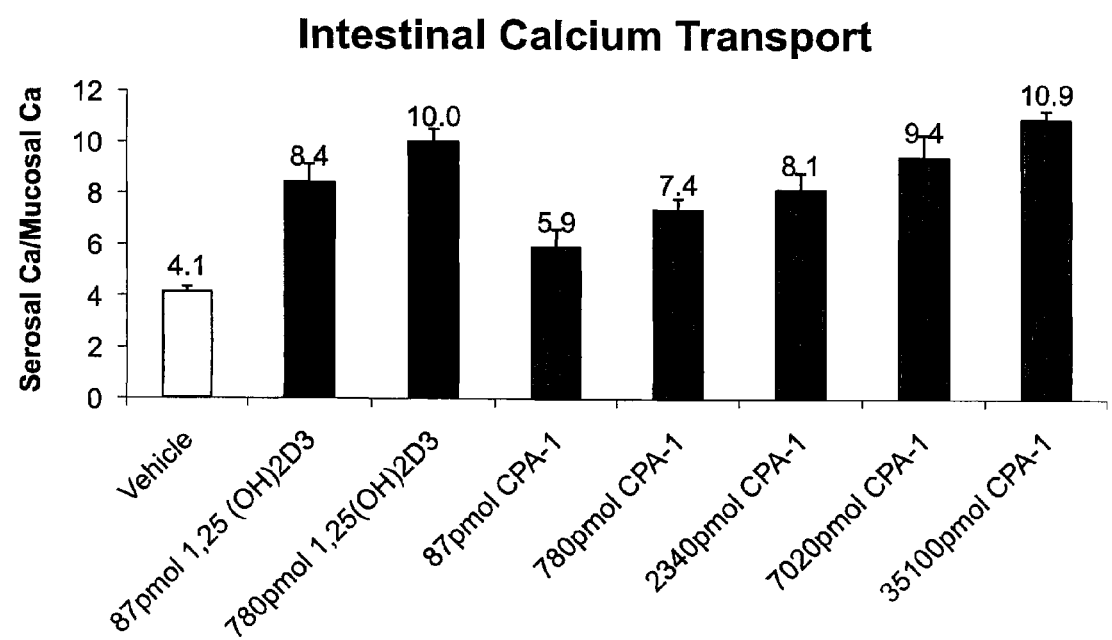

FIG. 5 shows that CPA-1 is quite potent, as compared to that of 1,25-dihydroxyvitamin $D_3$ (1,25$(OH)_2D_3$), the natural hormone, in stimulating intestinal calcium transport. CPA-1 is only about 20 times less potent than 1,25(OH)$_2$D$_3$ in promoting active calcium transport across the gut.

Figure 4:
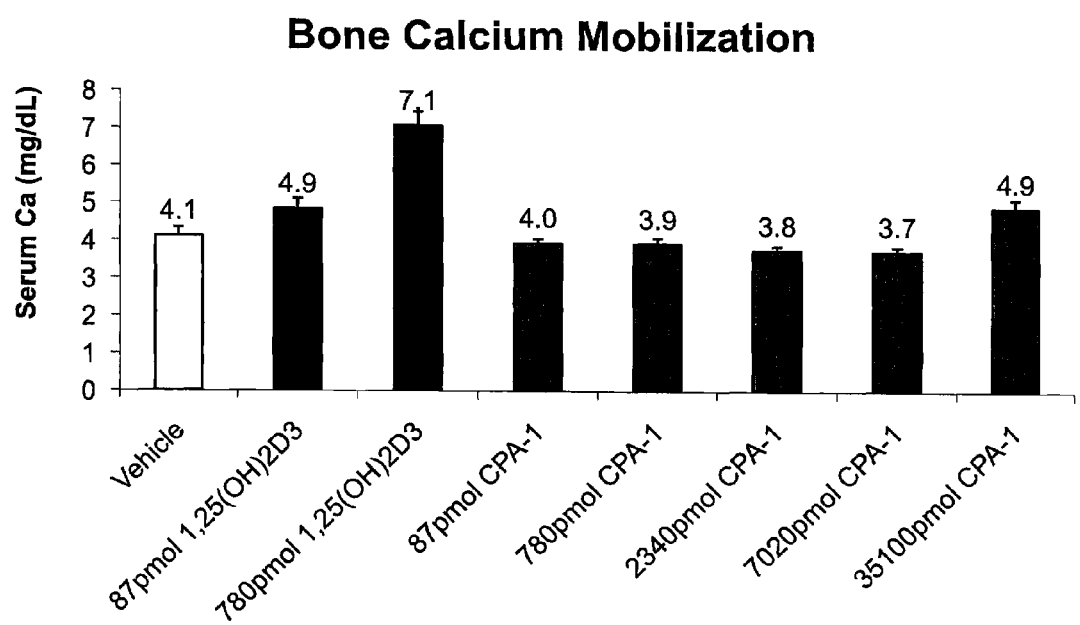

FIG. 4 demonstrates that CPA-1 has relatively low bone calcium mobilization activity, as compared to 1,25(OH)$_2$D$_3$. CPA-1 is less potent than the native hormone in releasing bone calcium stores as little to no activity is observed until 35,100 pmol/rat is administered; whereas, significant increases in serum calcium are observed at 87 pmol and at 780 pmol when the native hormone is given. Thus, CPA-1 is about 400 times less potent than 1,25(OH)$_2$D$_3$ in releasing bone calcium stores.

Figure 2:
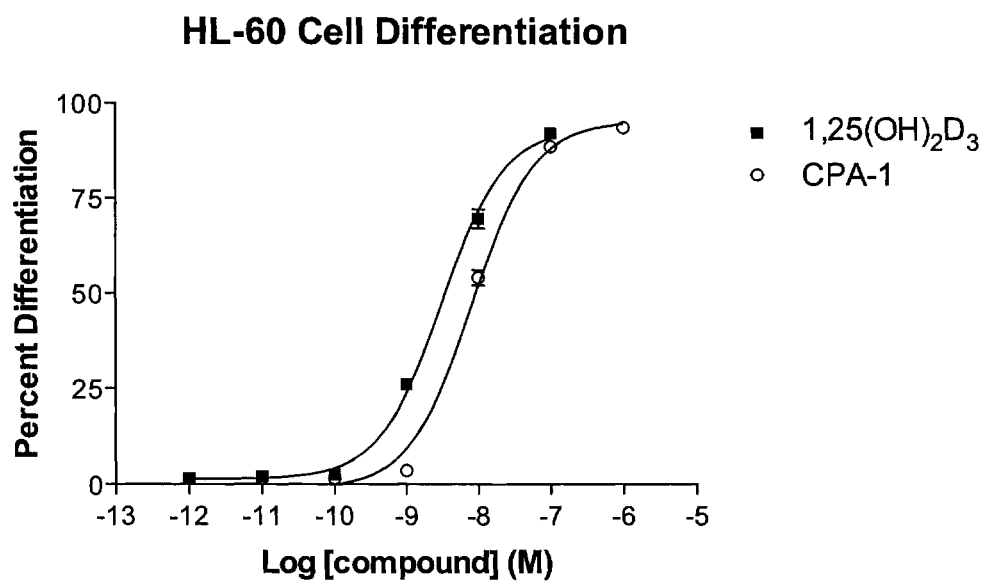

FIG. 2 illustrates that CPA-1 has the same high potency as 1,25(OH)$_2$D$_3$ on HL-60 cell differentiation, making it an excellent candidate for the treatment of a cancer, especially for the prevention or treatment of leukemia, colon cancer, breast cancer, skin cancer and prostate cancer.

Figure 3:
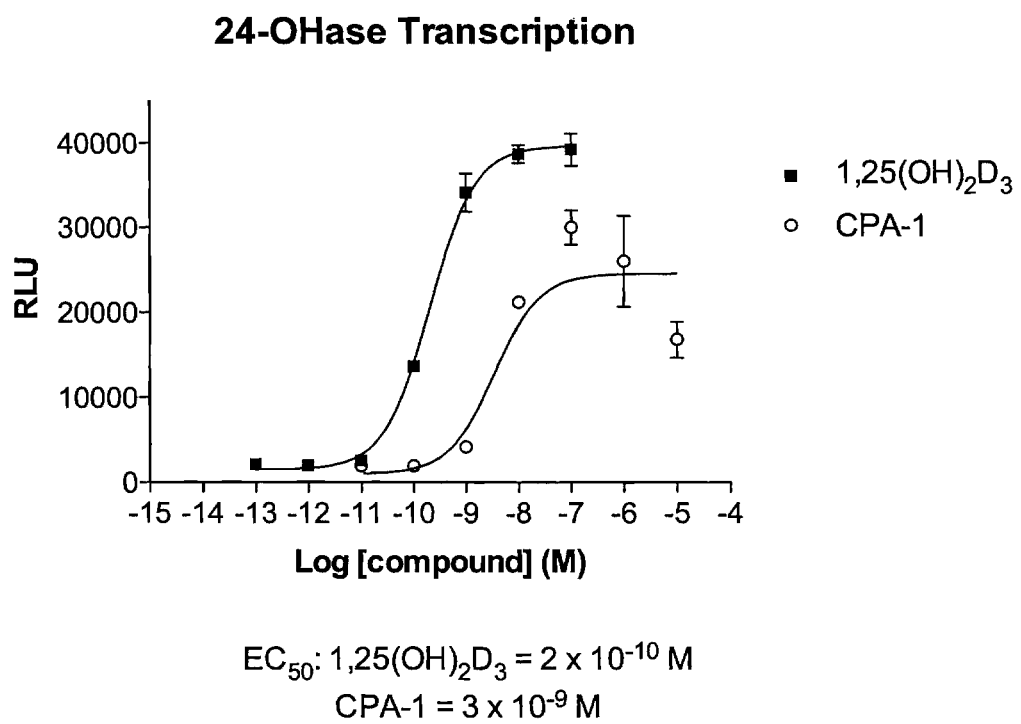

FIG. 3 illustrates that the compound CPA-1 has less transcriptional activity than 1α,25-dihydroxyvitamin D$_3$ in bone cells. In bone cells. CPA-1 is about 10 times less potent than 1,25(OH)$_2$D$_3$ in increasing transcription of the 24-hydroxylase gene. This result, together with the cell differentiation activity of FIG. 2, suggests that CPA-1 will be very effective in treating the above referred to cancers because it has direct cellular activity in causing cell differentiation, gene transcription, and in suppressing cell growth.

Experimental Methods

The compounds of the invention were prepared and studied using the following methods.
Vitamin D Receptor Binding
  Test Material
  Protein Source
  Full-length recombinant rat receptor was expressed in *E. coli* BL21 (DE3) Codon Plus RIL cells and purified to homogeneity using two different column chromatography systems. The first system was a nickel affinity resin that utilizes the C-terminal histidine tag on this protein. The protein that was eluted from this resin was further purified using ion exchange chromatography (S-Sepharose Fast Flow). Aliquots of the purified protein were quick frozen in liquid nitrogen and stored at −80° C. until use. For use in binding assays, the protein was diluted in TEDK$_{50}$ (50 mM Tris, 1.5 mM EDTA, pH7.4, 5 mM DTT, 150 mM KCl) with 0.1% Chaps detergent. The receptor protein and ligand concentration was optimized such that no more than 20% of the added radiolabeled ligand was bound to the receptor.
  Study Drugs
  Unlabeled ligands were dissolved in ethanol and the concentrations determined using UV spectrophotometry (1,25 (OH)$_2$D$_3$: molar extinction coefficient=18,200 and λ$_{max}$=265 nm). Radiolabeled ligand ($^3$H-1,25(OH)$_2$D$_3$, ~159 Ci/mmole) was added in ethanol at a final concentration of 1 nM.
  Assay Conditions
  Radiolabeled and unlabeled ligands were added to 100 mcl of the diluted protein at a final ethanol concentration of ≤10%, mixed and incubated overnight on ice to reach binding equilibrium. The following day, 100 mcl of hydroxylapatite slurry (50%) was added to each tube and mixed at 10-minute intervals for 30 minutes. The hydroxylapaptite was collected by centrifugation and then washed three times with Tris-EDTA buffer (50 mM Tris, 1.5 mM EDTA, pH 7.4) containing 0.5% Titron X-100. After the final wash, the pellets were transferred to scintillation vials containing 4 ml of Biosafe II scintillation cocktail, mixed and placed in a scintillation counter. Total binding was determined from the tubes containing only radiolabeled ligand.
HL-60 Differentiation
  Test Material
  Study Drugs
  The study drugs were dissolved in ethanol and the concentrations determined using UV spectrophotometry. Serial dilutions were prepared so that a range of drug concentrations could be tested without changing the final concentration of ethanol (≤0.2%) present in the cell cultures.
  Cells
  Human promyelocytic leukemia (HL60) cells were grown in RPMI-1640 medium containing 10% fetal bovine serum. The cells were incubated at 37° C. in the presence of 5% CO$_2$.
  Assay Conditions
  HL60 cells were plated at 1.2×10$^5$ cells/ml. Eighteen hours after plating, cells in duplicate were treated with drug. Four days later, the cells were harvested and a nitro blue tetrazolium reduction assay was performed (Collins et al., 1979; J. Exp. Med. 149:969-974). The percentage of differentiated cells was determined by counting a total of 200 cells and recording the number that contained intracellular black-blue formazan deposits. Verification of differentiation to monocytic cells was determined by measuring phagocytic activity (data not shown).
In Vitro Transcription Assay
  Transcription activity was measured in ROS 17/2.8 (bone) cells that were stably transfected with a 24-hydroxylase (24 Ohase) gene promoter upstream of a luciferase reporter gene (Arbour et al., 1998). Cells were given a range of doses. Sixteen hours after dosing the cells were harvested and luciferase activities were measured using a luminometer. RLU=relative luciferase units.
Intestinal Calcium Transport and Bone Calcium Mobilization
  Male, weanling Sprague-Dawley rats were placed on Diet 11 (Suda et al, J. Nutr. 100:1049, 1970) (0.47% Ca)+vitamins AEK for one week followed by Diet 11 (0.02% Ca)+vitamins AEK for 3 weeks. The rats were then switched to the same diet containing 0.47% Ca for one week followed by two weeks on the same diet containing 0.02% Ca. Dose administration began during the last week on 0.02% calcium diet. Four consecutive ip doses were given approximately 24 hours apart. Twenty-four hours after the last dose, blood was collected from the severed neck and the concentration of serum calcium determined by atomic absorption spectrometry as a measure of bone calcium mobilization. The first 10 cm of the intestine was also collected for intestinal calcium transport analysis using the everted gut sac method.

Interpretation of Data

VDR binding, HL60 cell differentiation, and transcription activity. CPA-1 (K$_i$=3×10$^{-9}$M) has slightly less activity than the natural hormone 1α,25-dihydroxyvitamin D$_3$ (K$_i$=2×10$^{-11}$M) in its ability to compete with [$^3$H]-1,25(OH)$_2$D$_3$ for binding to the full-length recombinant rat vitamin D receptor (FIG. 1). CPA-1 has the same high potency (EC$_{50}$=3×10$^{-9}$M) in its ability (efficacy or potency) to promote HL60 differentiation as compared to 1α, 25-dihydroxyvitamin D$_3$ (EC$_{50}$=2×10$^{-9}$M) (See FIG. 2). Also, compound CPA-1 (EC$_{50}$=3×10$^{-9}$M) has about 10 times less transcriptional activity in hone cells than 1α,25-dihydroxyvitamin D$_3$ (EC$_{50}$=2×10$^{-10}$M) (See FIG. 3). These data indicate that CPA-1 will have significant activity as an anti-cancer agent, especially for preventing or treating leukemia, colon cancer, breast cancer, skin cancer and prostate cancer because it has direct cellular activity in causing cell differentiation and in suppressing cell growth.

Calcium mobilization from bone and intestinal calcium absorption in vitamin D-deficient animals. Using vitamin D-deficient rats on a low calcium diet (0.02%), the activities of CPA-1. and 1,25(OH)$_2$D$_3$ in intestine and bone were tested. As expected, the native hormone (1,25(OH)$_2$D$_3$) increased serum calcium levels at both the 87 pmol and 780 pmol dosages tested (FIG. 4). FIG. 4 also shows that CPA-1 has significantly less activity in mobilizing calcium from bone than 1,25(OH)$_2$D$_3$. Administration of CPA-1. at 87 pmol/day, 780 pmol/day, 2,340 pmol/day and 7,020 pmol/day for 4 consecutive days resulted in little or no mobilization of bone calcium. CPA-1 is less potent than the native hormone in releasing bone calcium stores as little to no activity is observed until 35,100 pmol/rat is administered; whereas, significant increases in serum calcium are observed at both 87 pmol and 780 pmol when the native hormone is given.

Intestinal calcium transport was evaluated in the same groups of animals using the everted gut sac method (FIG. 5). These results show that the compound CPA-1 is about 20 times less potent in promoting intestinal calcium transport activity when administered at the recommended lower dosages, as compared to 1,25(OH)$_2$D$_3$, but its activity increases with increasing doses in a dose dependent manner. Thus, it may be concluded that CPA-1 has relatively high intestinal calcium transport activity at the tested doses.

These results further illustrate that CPA-1 is an excellent candidate for numerous human therapies as described herein. CPA-1 is an excellent candidate for treating a cancer because: (1) it has significant VDR binding, transcription activity and cellular differentiation activity; (2) it has low risk of hypercalcemic liability unlike 1,25(OH)$_2$D$_3$; and (3) it is easily synthesized.

For prevention and/or treatment purposes, the compounds of this invention defined by formula I and Ia may be formulated for pharmaceutical applications as a solution in innocuous solvents, or as an emulsion, suspension or dispersion in suitable solvents or carriers, or as pills, tablets or capsules, together with solid carriers, according to conventional methods known in the art. Any such formulations may also contain other pharmaceutically-acceptable and non-toxic excipients such as stabilizers, anti-oxidants, binders, coloring agents or emulsifying or taste-modifying agents.

The compounds of formula I and particularly CPA-1 of formula Ia, may be administered orally, topically, parenterally, rectally, nasally, sublingually, or transdermally. The compound is advantageously administered by injection or by intravenous infusion or suitable sterile solutions, or in the form of liquid or solid doses via the alimentary canal, or in the form of creams, ointments, patches, or similar vehicles suitable for transdermal applications. A dose of from 0.01 μg to 1000 μg per day of the compounds I, particularly CPA-1, preferably from about 0.1 μg to about 500 μg per day, is appropriate for prevention and/or treatment purposes, such dose being adjusted according to the disease to be treated, its severity and the response of the subject as is well understood in the art. Since the compound exhibits specificity of action, it may be suitably administered alone, or together with graded doses of another active vitamin D compound—e.g. 1α-hydroxyvitamin D$_2$ or D$_3$, or 1α,25-dihydroxyvitamin D$_3$—in situations where different degrees of bone mineral mobilization and calcium transport stimulation is found to be advantageous.

Compositions for use in the above-mentioned treatments comprise an effective amount of the compounds I, particularly CPA-1, as defined by the above formula I and Ia as the active ingredient, and a suitable carrier. An effective amount of such compound for use in accordance with this invention is from about 0.01 μg to about 1000 μg per gm of composition, preferably from about 0.1 μg to about 500 μg per gram of composition, and may be administered topically, transdermally, orally, rectally, nasally, sublingually or parenterally in dosages of from about 0.01 μg/day to about 1000 μg/day, and preferably from about 0.1 μg/day to about 500 μg/day.

The compounds I, particularly CPA-1, may be formulated as creams, lotions, ointments, topical patches, pills, capsules or tablets, suppositories, aerosols, or in liquid form as solutions, emulsions, dispersions, or suspensions in pharmaceutically innocuous and acceptable solvent or oils, and such preparations may contain in addition other pharmaceutically innocuous or beneficial components, such as stabilizers, antioxidants, emulsifiers, coloring agents, binders or taste-modifying agents.

The compounds I, particularly CPA-1, may be advantageously administered in amounts sufficient to effect the differentiation of promyelocytes to normal macrophages. Dosages as described above are suitable, it being understood that the amounts given are to be adjusted in accordance with the severity of the disease, and the condition and response of the subject as is well understood in the art.

The formulations of the present invention comprise an active ingredient in association with a pharmaceutically acceptable carrier therefore and optionally other therapeutic ingredients. The carrier must be "acceptable" in the sense of being compatible with the other ingredients of the formulations and not deleterious to the recipient thereof.

Formulations of the present invention suitable for oral administration may be in the form of discrete units as capsules, sachets, tablets or lozenges, each containing a predetermined amount of the active ingredient; in the form of a powder or granules; in the form of a solution or a suspension in an aqueous liquid or non-aqueous liquid; or in the form of an oil-in-water emulsion or a water-in-oil emulsion.

Formulations for rectal administration may be in the form of a suppository incorporating the active ingredient and carrier such as cocoa butter, or in the form of an enema.

Formulations suitable for parenteral administration conveniently comprise a sterile oily or aqueous preparation of the active ingredient which is preferably isotonic with the blood of the recipient.

Formulations suitable for topical administration include liquid or semi-liquid preparations such as liniments, lotions, applicants, oil-in-water or water-in-oil emulsions such as creams, ointments or pastes; or solutions or suspensions such as drops; or as sprays.

For nasal administration, inhalation of powder, self-propelling or spray formulations, dispensed with a spray can, a nebulizer or an atomizer can be used. The formulations, when dispensed, preferably have a particle size in the range of 10 to 100μ.

The formulations may conveniently be presented in dosage unit form and may be prepared by any of the methods well known in the art of pharmacy. By the term "dosage unit" is meant a unitary, i.e. a single dose which is capable of being administered to a patient as a physically and chemically stable unit dose comprising either the active ingredient as such or a mixture of it with solid or liquid pharmaceutical diluents or carriers.

We claim:
1. A compound of the formula:

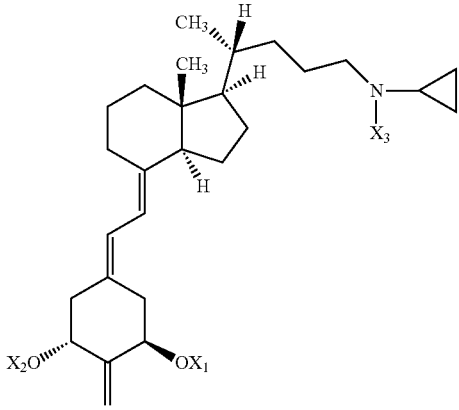

where $X_1$, $X_2$, and $X_3$, are the same or different and are each selected from the group consisting of hydrogen and a hydroxy-protecting group.

2. The compound of claim 1 wherein $X_1$ is hydrogen.

3. The compound of claim 1 wherein $X_1$ and $X_2$ are both t-butyldimethylsilyl.

4. The compound of claim 1 wherein $X_3$ is t-bilutyloxycarbonyl.

5. A pharmaceutical composition containing an effective amount of at least one compound as claimed in claim 1 together with a pharmaceutically acceptable excipient.

6. The pharmaceutical composition of claim 5 wherein said effective amount is about 0.01 µg to about 1000 µg per gram of the composition.

7. The pharmaceutical composition of claim 5 wherein said effective amount is about 0.1 µg to about 500 µg per gram of the composition.

8. A compound of the formula:

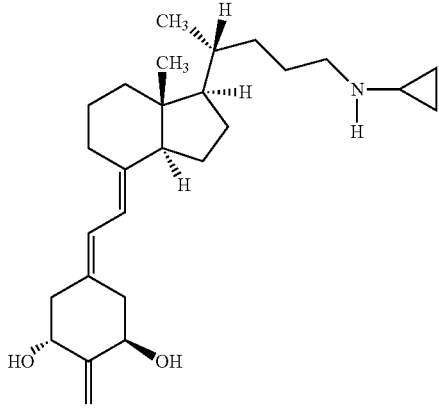

and named N-cyclopropyl-(20R)-2-methylene-19,26,27-trinor-25-aza-1α-hydroxyvitamin $D_3$.

9. A pharmaceutical composition containing an effective amount of N-cyclopropyl-(20R)-2-methylene-19,26,27-trinor-25-aza-1α-hydroxyvitamin $D_3$ together with a pharmaceutically acceptable excipient.

10. The pharmaceutical composition of claim 9 wherein said effective amount is about 0.01 µg to about 1000 µg per gram of the composition.

11. The pharmaceutical composition of claim 9 wherein said effective amount is about 0.1 µg to about 500 µg per gram of the composition.

12. A method of treating a disease selected from the group consisting of leukemia, colon cancer, breast cancer, skin cancer or prostate cancer comprising administering to a subject with said disease an effective amount of a N-cyclopropyl-(20R)-2-methylene-19,26,27-trinor-25-aza-vitamin D analog of the formula:

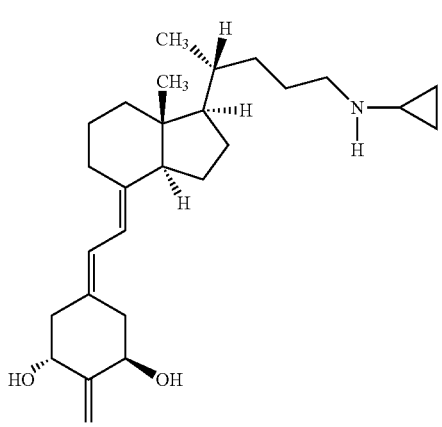

and named N-cyclopropyl-(20R)-2-methylene-19,26,27-trinor-25-aza-1α-hydroxyvitamin $D_3$.

13. The method of claim 12 wherein the vitamin D analog is administered orally.

14. The method of claim 12 wherein the vitamin D analog is administered parenterally.

15. The method of claim 12 wherein the vitamin D analog is administered transdermally.

16. The method of claim 12 wherein the vitamin D analog is administered rectally.

17. The method of claim 12 wherein the vitamin D analog is administered nasally.

18. The method of claim 12 wherein the vitamin D analog is administered sublingually.

19. The method of claim 12 wherein the vitamin D analog is administered in a dosage of from about 0.01µg/day to about 1000 µg/day.

20. A compound of the formula:

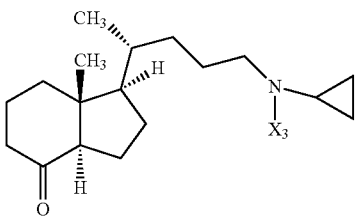

where $X_3$ is selected from the group consisting of hydrogen and a hydroxy-protecting group.

21. The compound of claim 20 wherein $X_3$ is hydrogen.

22. The compound of claim 20 wherein $X_3$ is tert-butyloxycarbonyl.

23. A compound of the formula:

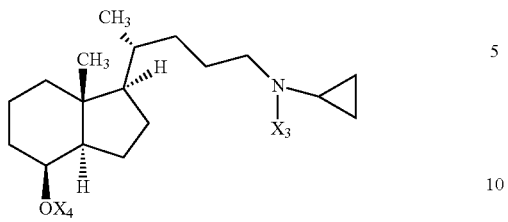

where $X_3$ and $X_4$ are the same or different and are each selected from the group consisting of hydrogen and a hydroxy-protecting group.

24. The compound of claim 23 wherein $X_3$ is hydrogen.
25. The compound of claim 23 wherein $X_4$ is hydrogen,
26. The compound of claim 23 wherein $X_3$ is hydrogen and $X_4$ is a triethylsilyl group.
27. The compound of claim 23 wherein $X_4$ is hydrogen and $X_3$ is tert-butyloxycarbonyl.
28. The compound of claim 23 wherein $X_3$ is tert-butyloxycarbonyl, and $X_4$ is a triethyslilyl group.

* * * * *